United States Patent [19]

Meller et al.

[11] Patent Number: 5,628,963
[45] Date of Patent: May 13, 1997

[54] APPARATUS FOR QUANITATIVE EVALUATION OF AGGLUTINATION REACTIONS

[75] Inventors: Paul Meller, Langen; Susanne Scheuermann, Bad Homburg; Matthias Zimmermann, Sulzbach, all of Germany

[73] Assignee: Behringwerke Aktiengesellschaft, Marburg, Germany

[21] Appl. No.: 477,632

[22] Filed: Jun. 7, 1995

Related U.S. Application Data

[60] Continuation of Ser. No. 44,474, Apr. 9, 1993, which is a division of Ser. No. 796,247, Nov. 21, 1991, abandoned.

[30] Foreign Application Priority Data

Nov. 23, 1990 [DE] Germany ............... 40 37 245.6

[51] Int. Cl.[6] .................................................. G01N 21/49
[52] U.S. Cl. ..................... 422/73; 422/82.09; 356/39; 356/338
[58] Field of Search .................. 422/64, 73, 82.09; 366/209, 213, 219; 356/39, 337, 338, 244; 436/45, 46, 909

[56] References Cited

U.S. PATENT DOCUMENTS 4,109,319  8/1978  Brandt ................................ 366/219
5,051,370  9/1991  Schulze et al. ..................... 436/165

FOREIGN PATENT DOCUMENTS 0107580   5/1984   European Pat. Off. .
0402795  12/1990   European Pat. Off. .
3919260   6/1989   Germany .
4019299   8/1991   Germany .

OTHER PUBLICATIONS

Fischer Scientific, product catalogue, pp. 712 and 973 (1988).

Perry, R.H., "Perry's Chemical Engineer's Handbook", 6th ed., New York, McGraw-Hill Book Company, 1984, Chapter 24, p. 49.

Primary Examiner—Jeffrey Snay
Attorney, Agent, or Firm—Finnegan, Henderson, Farabow, Garrett & Dunner, L.L.P.

[57] ABSTRACT

In the method for quantitative evaluation of agglutination reactions between a reagent and a biological fluid to be examined, the reagent and the biological fluid are intimately mixed by a horizontal circular movement. The agglutinates formed in the mixture while the circular movement is maintained are optically imaged thereafter on a ground glass plate, and the image is evaluated using an electronic evaluation device.

7 Claims, 2 Drawing Sheets

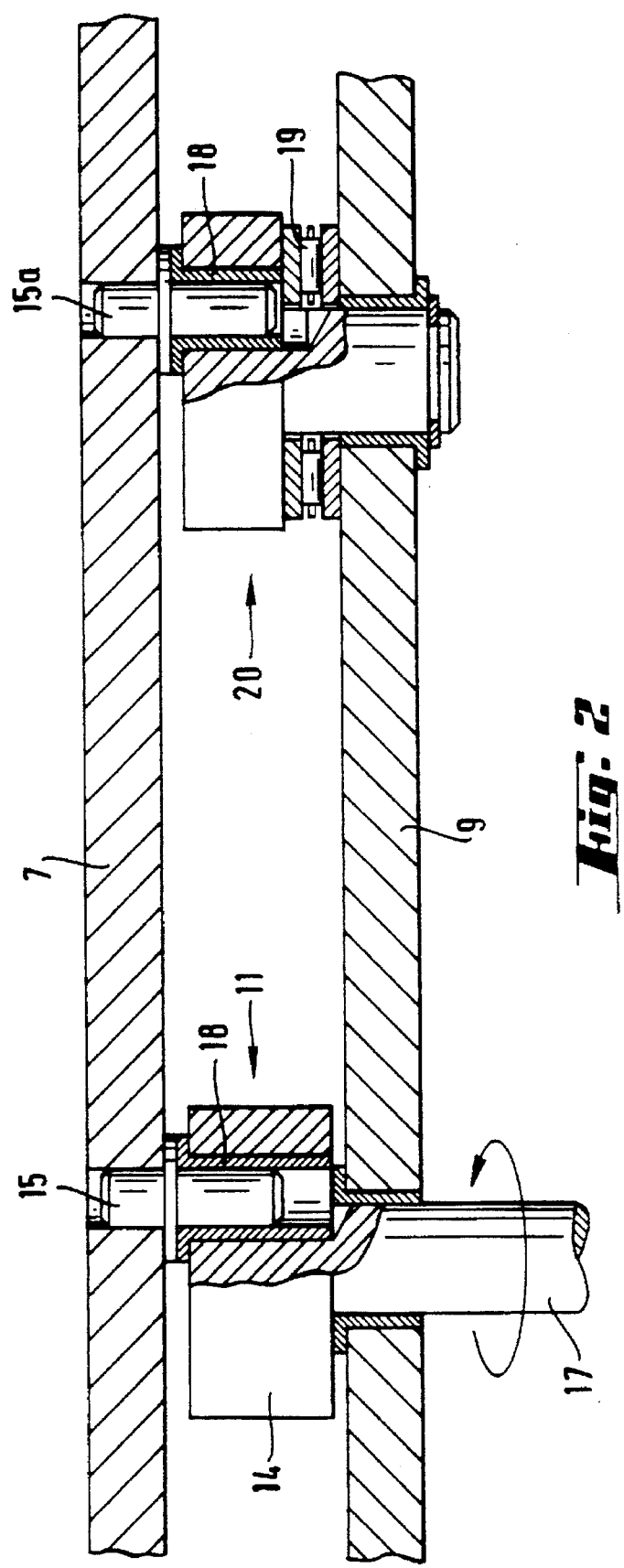

APPARATUS FOR QUANTITATIVE EVALUATION OF AGGLUTINATION REACTIONS

This is a continuation of application Ser. No. 08/044,474 filed Apr. 9, 1993, which is a divisional of Ser. No. 07/796,247 filed Nov. 21, 1991, now abandoned.

BACKGROUND OF THE INVENTION

1. Field of the Invention

The subject matter of the invention is a method for quantitative evaluation of agglutination reactions between a reagent and a biological fluid to be examined. The subject matter of the invention is, furthermore, an apparatus for carrying out the method, which is composed of an optical measuring arrangement of a light source, condenser, detecting device for a measuring field, objective and ground glass plate with an optoelectronic evaluating device.

2. Description of the Related Art

Agglutination reactions as a diagnostic method serve to protect and diagnose specific diseases such as myocardial infarcts, inflammations, rheumatoid factors etc. In the test required for the diagnosis, biological fluid such as blood serum is mixed manually with a specific antigen on a stained assay plate. After the reaction, the result is visually checked and evaluated diagnostically. In this process, the formation of agglutinates can be used to draw conclusions on the existence of corresponding antigens or antibodies. Apart from the specific biological properties of the proteins used, the significance of a positive or negative reaction depends strongly in this case on the judgment and experience of the particular experimenter or member of the laboratory staff. The disadvantage of this mode of procedure resides in that it is highly dependent upon the experience of the observer, there is limited measuring range and only yes/no statements on the result of the reaction are possible as a rule. Typically, no further-reaching statements can be made about quantifying the reaction.

Furthermore, DE-A-3,919,260 discloses a method for quantitative evaluation of agglutination reactions in which the agglutinates formed are detected optoelectronically and integrated over a fixed time interval. The thorough physical mixing of the reactants inside the fluid is performed by superimposing a tumbling movement and a rotational movement. A translation movement is superimposed on the tumbling movement during the optoelectronic measurement. The method permits the measurement of concentration-dependent, kinetic reaction processes and the quantifying of the agglutination reaction with the aid of appropriately constructed calibration curves. The disadvantage of this measurement method resides in the combination of a plurality of complicated processes of movement for the thorough mixing of the components inside the fluid, in the placing of the material to be measured in the beam path and in the superimposition of the tumbling movement with a translational movement during the optoelectronic measurement.

SUMMARY OF THE INVENTION

The invention is intended to provide a remedy here. The object is achieved by means of a method, wherein the reagent and the biological fluid are intimately mixed by a horizontal circular movement, the agglutinates formed in the mixture while the circular movement is maintained are optically imaged thereafter on a ground glass plate, and the image is evaluated using an electronic evaluating device.

In order to carry out the method according to the invention, an apparatus of the type mentioned earlier was further provided, wherein the detecting device is composed of a movable plate which is connected to a drive motor via a coupling arranged offset parallel to the motor shaft, and to a support via connecting elements, and which has at least one cutout for a measuring field. The coupling can be composed of a disc, arranged on the motor shaft, which has an eccentrically arranged pin for connecting the motor and plate.

The method according to the invention is simpler than the known method. This also applies to the measuring apparatus. To realize in a measuring instrument the movement required for the mixing is very simple and cost effective. In particular, due to the appropriate configuration and mounting of the detecting device for the measuring fields it is possible for a plurality of fields to be arranged thereon and simultaneously detected and evaluated. As a result, it is possible, for example, to carry out, simultaneously within a measuring cycle, measurements of undiluted reaction fluid, one or more dilution stages and positive/negative control measurements. The optical calibration of the measuring apparatus can be performed by particles of defined size. The apparatus enables a precise and reproducible determination of the start of an agglutination reaction, and the enumeration of the agglutinates formed on a plurality of channels. Thus, for example, in the case of the use of an antigen that is immobilized on latex, it is possible to determine the lower limit of detection at 30 IU/ml for antistreptolysin, at 4 IU/ml for rheumatoid factor, and at 0.3 mg/dl for C-reactive protein.

Given appropriate choice of the rotational frequency and amplitude of, for example, 1 to 5 Hz and 5 to 15 mm of the horizontal circular movement of the measuring field, a complete thorough mixing of the biological fluid with the antigen or the antibody is guaranteed in common with the position of the measuring field in the beam path of the optical measuring arrangement.

BRIEF DESCRIPTION OF THE DRAWINGS

The invention is explained in more detail below with reference to the figures, wherein:

FIG. 2 illustrates an alternative embodiment of the stabilization of the detecting device for the measuring fields in accordance with the present invention.

DETAILED DESCRIPTION OF THE PREFERRED EMBODIMENTS

Figure 1:
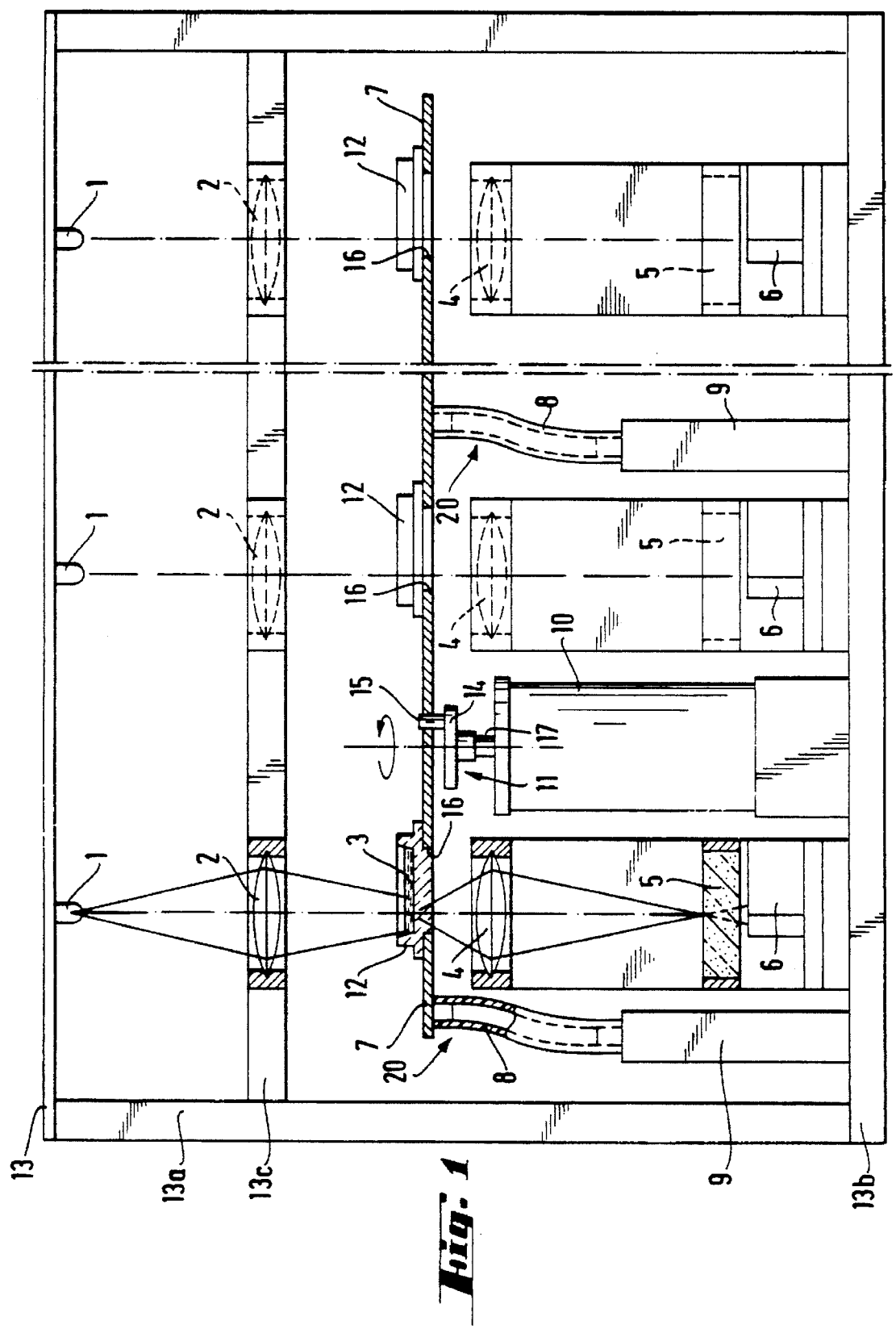
FIG. 1 illustrates a diagrammatic representation of an apparatus for carrying out the method in accordance with the present invention.

As illustrated in FIG. 1, arranged in a frame 13, 13a, 13b, 13c is an optical measuring arrangement of a light source 1, condenser 2, detecting device for the measuring field 12, objective 4 and ground glass plate 5 with an optoelectronic evaluating device 6. The detecting device is composed of a plate 7, which is connected to a drive motor 10 via a coupling 11. The coupling 11 can be composed of a disc 14, arranged on the motor shaft 17, and a pin 15 which is arranged eccentrically on the disc 14 and connected in an articulated fashion to the plate 7. Furthermore, the plate 7 is connected to supports 9 via connecting elements 20, for example via elastic parts 8 or as illustrates in FIG. 2, via pins 15a guided through thrust bearings 19 and bushes 18. The supports 9 can be composed of props or a plate that are attached to the frame 13, 13a, 13b, 13c. The plate 7 has at least one cutout 16 for a measuring field 12, on which are located the reaction fluid 3, composed of biological fluid, and reagent. As indicated, a plurality of measuring fields 12 can be arranged on the plate 7. Transparent specimen slides or the like are suitable as measuring field 12. The start of the reaction, the total reaction time and the quantity of the agglutinates formed can be measured using the optoelectronic evaluation device 6.

As discussed earlier, the invention has been found to work well when the rotational frequency and amplitude are in the range 1 to 5 Hz and 5 to 15 mm of horizontal circular movement of the measuring field, respectively.

What is claimed is:

1. A quantitative evaluation apparatus comprising:

a condenser;

means for holding a transparent specimen slide, the holding means including a movable plate having a cutout defining a measuring field;

an objective;

a transparent plate;

an optoelectric evaluation device;

a frame;

a support connected to the movable plate via a connecting element, the support including a support plate that is connected to the frame, the movable plate being supported on the support plate via pins guided through thrust bearings;

a light source constructed and positioned so as to emanate a beam of light along a path sequentially through the condenser, the measuring field, the objective, the transparent plate and to the optoelectric evaluation device; and means for orbitally agitating in a single plane the holding means while the measuring field is in the path, the agitating means including a drive motor having a shaft, and a coupling connecting the drive motor to the movable plate, the coupling being arranged offset from and parallel to the motor shaft.

2. The apparatus as claimed in claim 1, wherein the coupling includes a disc, arranged on the motor shaft, the disc having an eccentrically arranged pin for engaging the movable plate.

3. The apparatus of claim 1 wherein the transparent plate is constructed of ground glass.

4. The apparatus of claim 1 wherein the motor and coupling are configured to rotate the measuring field with an amplitude of 5 to 15 mm of horizontal circular movement and at a frequency of between 1 and 5 Hz.

5. A quantitative evaluation apparatus comprising:

a condenser;

a movable plate having a cutout defining a measuring field;

an objective;

a transparent plate;

an optoelectric evaluation device;

a frame;

a support connected to the movable plate via a connecting element, the support including a support plate that is connected to the frame, the movable plate being supported on the support plate via pins guided through thrust bearings;

a light source constructed and positioned so as to emanate a beam of light along a path sequentially through the condenser, the measuring field, the objective, the transparent plate and to the optoelectric evaluation device; and means for orbitally agitating in a single plane a sample in the measuring field while the measuring field is in the path, the agitating means including a drive motor having a shaft, and a coupling connecting the drive motor to the movable plate, the coupling being arranged offset from and parallel to the motor shaft.

6. The apparatus of claim 5 wherein a transparent specimen slide is located in the measuring field.

7. The apparatus of claim 5 wherein the motor and coupling are configured to rotate the measuring field with an amplitude of 5 to 15 mm of horizontal circular movement and at a frequency of between 1 and 5 Hz.

* * * * *